United States Patent [19]

Spurlin et al.

[11] Patent Number: 4,575,433
[45] Date of Patent: Mar. 11, 1986

[54] METHOD OF GENERATING CHEMILUMINESCENT LIGHT

[75] Inventors: Stanford R. Spurlin; Edward S. Yeung, both of Ames, Iowa

[73] Assignee: Iowa State University Research Foundation, Inc., Ames, Iowa

[21] Appl. No.: 688,553

[22] Filed: Jan. 3, 1985

Related U.S. Application Data

[62] Division of Ser. No. 462,532, Jan. 31, 1983.

[51] Int. Cl.⁴ .................. C09K 11/07; C09K 11/56; C09K 11/61; F21K 2/06
[52] U.S. Cl. ........................... 252/700; 362/34; 423/573 R; 423/573 G; 423/500; 423/567 R; 436/120; 436/121; 436/172
[58] Field of Search .............. 436/35, 119, 120, 121, 436/124, 172; 434/296; 250/458.1, 459.1, 493.1; 446/216; 252/700; 362/34; 423/573 R, 573 G, 567 R, 500

[56] References Cited

U.S. PATENT DOCUMENTS

| | | | |
|---|---|---|---|
| 3,213,440 | 10/1965 | Gesteland et al. | 252/700 X |
| 3,630,939 | 12/1971 | Schneider | 252/700 |
| 3,751,846 | 8/1973 | Benjamin | 446/219 X |
| 3,962,029 | 6/1976 | Wettermark et al. | 252/700 X |
| 4,098,639 | 7/1978 | Noreus et al. | 423/221 X |

OTHER PUBLICATIONS

Arnold et al., J. Appl. Phys., vol. 50, No. 3, pp. 1189–1194, 1979.
Chemical Week, Sep. 20, 1982, p. 61.

Primary Examiner—Barry S. Richman
Assistant Examiner—Robert J. Hill, Jr.
Attorney, Agent, or Firm—Zarley, McKee, Thomte, Voorhees & Sease

[57] ABSTRACT

A method of chemiluminescently determining a sulfide which is either hydrogen sulfide or methyl mercaptan by reacting the sulfide with chlorine dioxide at low pressure and under conditions which allow a longer reaction time in emission of a single photon for every two sulfide containing species, and thereafter, chemiluminescently detecting and determining the sulfide. The invention also relates not only to the detection method, but the novel chemical reaction that generates chemiluminescent light and a specifically designed chemiluminescence detection cell for the reaction.

3 Claims, 4 Drawing Figures

METHOD OF GENERATING CHEMILUMINESCENT LIGHT

GRANT REFERENCE

This invention was conceived and reduced to practice in part under a grant from the Department of Energy under Contract No. W-7405-eng.-82.

This is a division of application Ser. No. 462,532 filed Jan. 31, 1983.

BACKGROUND OF THE DISCLOSURE

The need for continuously monitoring a species like hydrogen sulfide and methyl mercaptan in the atmosphere is readily apparent because of the toxic nature of these compounds. It is particularly important in synfuel production and in geothermal energy utilization. Also, hydrogen sulfide is an impurity in synthesis gas which is used in the industrial production of methanol, methane, glycols and other hydrocarbons. Costly catalysts used in petrochemicals are readily "poisoned" unless the hydrogen sulfide level is below one part per million. Presently, hydrogen sulfide in air can be determined by colorimetry, conversion to metal sulfides and subsequent photometry, gas chromatography with flame photometric detectors, and ion-selective electrodes. The problem with all of these techniques is that for low concentration levels, they all require collecting the gas sample of interest over fairly long times followed by capture and concentration of hydrogen sulfide and some chemical preparation. Thus, they cannot achieve truly continuous monitoring.

It is therefore a primary objective of the present invention to provide not only a highly sensitive detection method for hydrogen sulfide and methyl mercaptan which will detect those at very low levels, even as low as one part per billion, but also to allow detection of those in a method which is truly continuous to allow continual monitoring of industrial reactions for the presence of potentially poisoning sulfide.

It is also an object of the present invention to provide not only a continuous, highly sensitive monitoring system for sulfide containing compounds, particularly hydrogen sulfide and methyl mercaptan, but also to provide a new chemical reaction which generates chemiluminescent light and allows the use of chemiluminescence technology to conduct the detection and determination method of the invention.

An even further objective of the invention is to provide a reaction cell which allows continuous monitoring and reaction for determining chemiluminescently the presence of potentially poisoning sulfide atoms.

The method, means and apparatus for accomplishing each of the above objectives will be apparent from the detailed description of the invention which will follow hereinafter.

SUMMARY OF THE INVENTION

A method of chemiluminescently determining sulfide, which can be continuously run in order to monitor industial reactions which might be poisoned by sulfide. The method involves use of the photon emitting reaction between hydrogen sulfide and/or methyl mercaptan and chlorine dioxide to provide emission of a single photon for every two sulfur containing species. The reaction is conducted at low pressure and under conditions to allow longer residence times to assure photon emission. In addition, the invention involves a specially designed reaction cell which assures that conditions will be correct for photon emission.

DETAILED DESCRIPTION OF THE INVENTION

Figure 1:
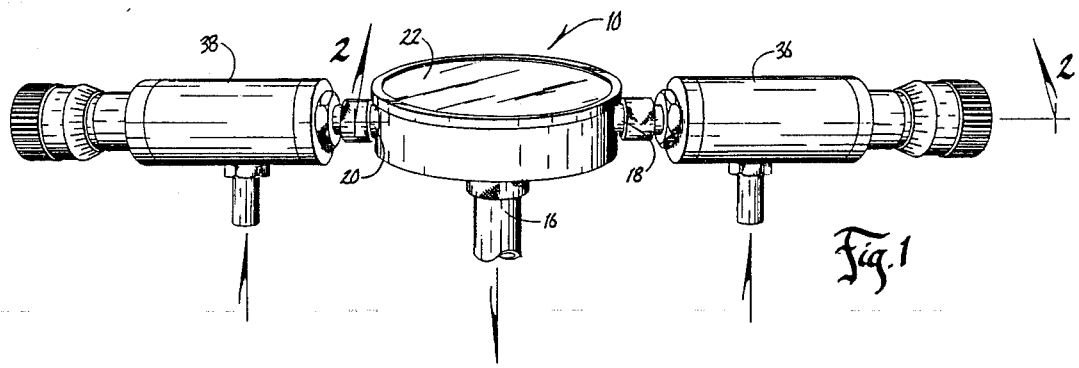
FIG. 1 is an elevated perspective view of the reaction cell of this invention, showing metering valves attached to each of the inlets.

Chemiluminescence under the right conditions is an extremely sensitive method for both qualitative and quanitative determination. The reactions for one can correlate the emissions of photons with each molecule of interest, and thus one can quanitatively and qualitatively determine very low levels of the presence of the molecule of interest, in this case, sulfur. Commonly the most widely used reagent is the gas phase of ozone (atomic oxygen). Unfortunately the reaction is not very selective, and compounds like sulfur dioxide, nitrogen oxides and unsaturated hydrocarbons all produce emissions that can interfere with the detection of hydrogen sulfide. It is apparent, therefore, that a selective detector should be based on emission from a species related chemically to the analyte, rather than the reagent.

In accordance with the process of this invention, the applicant has discovered that both hydrogen sulfide and methyl mercaptan will react with chlorine dioxide, at lower pressures, to provide a single photon for every two atoms of sulfur. This reaction has the capability of being chemiluminescently detected, because of the photon emission. The representative reaction for hydrogen sulfide is set forth below:

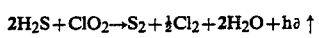

$$2H_2S + ClO_2 \rightarrow S_2 + \tfrac{1}{2}Cl_2 + 2H_2O + h\vartheta \uparrow$$

It can be seen that chlorine dioxide will react with the hydrogen sulfide, and similarly with methyl mercaptan to produce sulfur atoms which recombine to form electronically excited $S_2$ and in turn result in luminescence. This specificity is the key to the present invention.

It is desirable to the reaction of the invention that it be conducted generally at room conditions, i.e., from 18° C. to 30° C. and that it be conducted at low pressure. If the pressure is too high, the reaction will be quenched and photon emission will not occur. To minimize the effects of quenching, one must keep the reaction zone at the reduced pressures, that is, at 40 torr or below. The preferred pressure is from about 20 torr to about 40 torr. The most preferred pressure is within the range of about 25 torr to about 35 torr and the very most preferred at about 30 torr.

To maximize sensitivity despite this high order reaction, one must keep the volume of the reaction zone small and the reagent gas, ($ClO_2$), preferably in excess to assure complete reaction for quantitative analysis.

As heretofore mentioned, the invention relates not only to the novel photon emission reaction, but the method of chemiluminescently detecting sulfide, preferably on a continual monitoring basis, but also relates to a reaction cell suitable for continual on-line monitoring detection of sulfide.

Before discussing the details of the cell, a very brief mention, by way of background, of chemiluminescence detectors, may be appropriate. Chemiluminescence detection per se is, of course, known. It refers to the ability of materials to give off a faint glow during reactions with certain chemical compounds. The phenomenon is now effectively used in instrumental analysis techniques.

Figure 4:
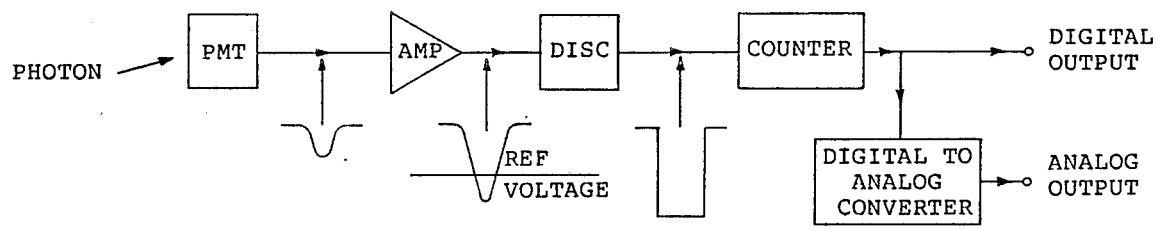
FIG. 4 is a block diagram to show the photon multiplier tube against which the quartz window of the cell of FIG. 3 is placed for chemiluminescence detection.

FIG. 4 represents a typical chemiluminescence detector, or photon counter. The output pulse from a photomultiplier tube (PMT) caused by a photon striking the PMT photo-cathode, is amplified and passed to a pulse height discriminator circuit. In the discriminator, the peak value of the pulse is compared to a reference voltage (discrimination level). If the pulse amplitude exceeds the discrimination level, the discriminator generates a standard pulse which is counted by the digital counter. If the input pulse to the discriminator has a peak amplitude which is less than the discrimination level, no output pulse is generated. This prevents the counting of spurious signals which are not photon related. Numerous available chemiluminescence detection photomultiplier counters, such as represented by the block diagram, are readily available commercially. For further details, see, EG&G, Princeton Applied Research brochure, entitled "Photocounting" published by Princeton Applied Research P. 0. Box 2565, Princeton, N.J., copyright 1980, printing No. T-335C-20M-3/80-CP, which is incorporated herein by reference. One satisfactory photomultiplier which has been used is a 56 DUVP photomultiplier tube from Amperex, of Hicksville, N.Y. A suitable counter is the EG&G Ortec 9315 photon counter with a 9325 EG&G amplifier-discriminator.

Figure 2:
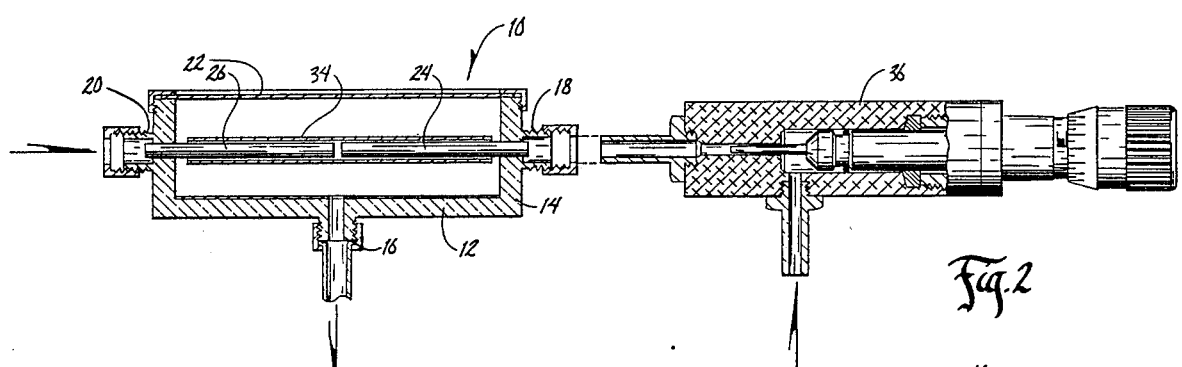
FIG. 2 is a sectional view along line 2—2 of FIG. 1.
Figure 3:
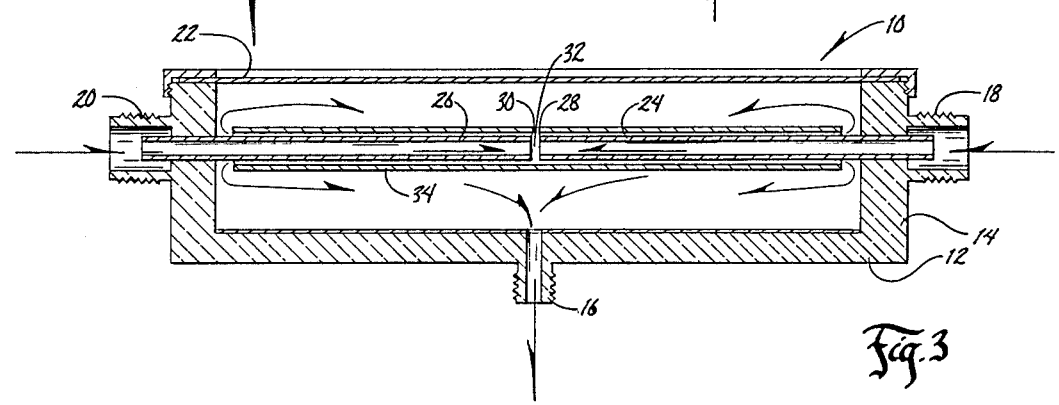
FIG. 3 is a sectional view, in elevation, through the reaction cell in order to show gas flow therein.

The reaction cell of the present invention is placed against the photomultiplier tube which senses the photon emissions from the reaction within the cell. The reaction cell 10 is illustrated in FIGS. 1–3, and is particularly well shown in the elevated sectional view of FIG. 3. It can be made of brass, nickel, stainless steel or aluminum. There, it can be seen that the cell 10 is comprised of a bottom wall 12, and a circular side wall 14. Bottom wall 12, at approximately its midpoint position, has an exit opening 16. At opposite sides, with respect to each other, and positioned in side wall 14 are two inlet openings 18 and 20. The side walls 14 at their upper portion terminate to provide an open top for the cell. However the open top is sealingly covered with a quartz window, or plate 22. Each of the opposed inlets 18 and 20 are provided with a quartz inlet tube 24, 26 which extends from the inlet end interiorally, with each terminating in an exit end 28 and 30 which is opposed to the exit end of the other, to define a turbulance gap, 32, therebetween.

As can best be seen in FIG. 3, a quartz sheath 34, is of a sufficient inside diameter to allow it to be snugly positioned over inlet tubes 24 and 26, and it covers the turbulance gap and also a portion of tubes 24 and 26.

Tubes 24 and 26 and window 22 are all made of quartz. This must be so because quartz is transparent to the emitted photon, and thus accurate photon counts will result.

In actual operation, the cell 10 may be connected at each of its respective inlets 18 and 20 to a pair of metering valves 36 and 38. Needle metering valves such as 36 are well known, but a section is shown through one in FIG. 2. The operator can simply adust the rate of in flow of gas by simply turning the dial on the right hand side of the metering valve 36. Since it does not form a part of the invention per se, it will not be described further.

When the unit is ready for operation, one of the inlets, for example, 18, is connected to a source of for example, chlorine dioxide. The other inlet 20 is connected to a source of, for example, hydrogen sulfide, or methyl mercaptan. The gases are then adjusted for suitable flow rates, and enter into respective inlet quartz tubes 24 and 26. Gas flow therein is indicated by the directional arrows of FIG. 3, until they meet at the turbulance gap 32. When the gases meet, they react. Exit line 16 allows the reacted gases to be swept away for continuous monitoring.

The gases meeting at the turbulance zone 32 must move somewhere. The only place that they can move is around the outside of the inlet tubes and along the interior wall of the quartz sheath 34, thus assuring a longer residence or contact time. The combined gases then move outwardly along the interior wall of the sheath 34 and eventually escape from the outer ends as depicted by the arrows at each end of the sheath 34. Thereafter, gases are swept away as indicated by the directional arrows adjacent the exit line 16. Pressure is maintained within the desired pressure range expressed earlier by control of the incoming flow rates and the diameter differential between the inlet tubes 24 and 26 and the inside diameter of the sheath tube 34.

It therefore can be seen that the reaction can be conducted in a manner which assures low pressure to assure that quenching will not occur, and with long residence or contact time. The top or exterior face of quartz window 22 is placed against the photomultiplier tube of FIG. 4 and photon sensing occurs.

It can be seen that because gases continuously can be let into the reaction cell, and continuously withdrawn via line 16, that a continuous monitoring reaction can occur. Thus, if one is, for example, running a petrochemical reaction whose catalyst can be poisoned by sulfide, the continuous monitoring can occur and immediately the chemiluminescence detector will sense the presence of sulfide poisoning.

The following example is offered to further illustrate, but not limit, the invention.

EXAMPLE

The inlet tubes 24, 26 are 1 mm i.d. quartz tubings aligned with the ends 0.5 mm apart. A sheath 34 based on a 3 mm d., 60 mm long quartz tube is used to define the reaction zone. The aperture for flow has an area given by the difference in cross-sectional areas of the tubes 24, 26 and the inside of 34. The use of quartz allows chemiluminescence below 320 nm to be observed through a ⅛ inch thick window 22. A mechanical pump (DuoSeal, Welch, Chicago, Ill.) provides the flow and is connected to the cell via exit line 16, after a cryogenic trap. The cell body is machined out of brass locally and is lined with aluminum foil (not shown) opposite the window 22 to enhance the collection of light. The reacting gases are introduced into the cell through metering valves attached at 36, 38. A fine metering valve (Nupro, Willoughby, Oh., type "S") packed with Teflon is used for $ClO_2$, and a stainless steel leak valve (Veeco, Plainview, N.Y., VVB=5-S) is used for the air-$H_2S$ mixtures. The effective aperture areas for the two at typical operating conditions are $1.6 \times 10^{-3}$ mm² and $9 \times 10^{-4}$ mm², respectively. One then determined the pressure in the reaction region, to be about 30 torr.

A 56 DUVP photomultiplier tube (represented by FIG. 4) (Amperex, Hicksville, N.Y.) is attached directly to the window 22 to provide a collection efficiency of about f/1. f/1 commonly refers to the ratio of the focal length to the diameter of a collection lens. Photon counts are registered by use of an Ortec (EG&G, Oakridge, Tenn.) 9315 photon counter and a 9325 amplifier-discriminator Spectral scans are obtained through a grating monochromator McPherson, Acton, Mass., Model 270) after passing through a lens system again with an f/1 collection efficiency.

$ClO_2$ was generated by the Bray method (Bray, W.Z. Phys. Chem. 1906, 54, 569–570) and stored under liquid nitrogen after the excess $Cl_2$ was removed by distillation. To assure a low pressure in the cylinder while in use, and to maintain an even flow of $ClO_2$, we used a methanol-water slush bath at $-10°$ C. A 0.2 ppm $H_2S$ in $N_2$ sample was obtained from Matheson (East Rutherford, N.J.).

The initial observation of chemiluminescence from the reaction between $ClO_2$ and $H_2S$ is crude but shows good potential for analytical applications. About 20 torr of $ClO_2$ is introduced into a side arm of the vacuum system. A vacuum stopcock separates this from the manifold filled with about 30 torr of $H_2S$. With the room lights off, mixing is allowed to occur by opening the stopcock. One can easily observe a bluish white glow traveling down the side arm as the mixing proceeds. Afterward, one can detect a coating of sulfur along the walls of the side arm. If, however, 300 torr of $ClO_2$ and 750 torr of $H_2S$ are used instead, no emission is readily detectable visually even though sulfur deposit is again formed. The formation of elemental sulfur hints at the likelihood of $S_2$ being the emitting species. The lack of observable luminescence at high pressures confirms the role of quenching and hence the need for a special flow cell. The visual detection points to the high sensitivity, especially since the $S_2$ emission is mainly in the ultraviolet region.

Further analytical testing has revealed that the system measures the total amount of $H_2S$ and $CH_3SH$ present. In particular, the photon counts were correlated with the $H_2S$ concentration in the following manner: The analytical calibration plot of measured intensity (photon counts per second) vs. the concentration of $H_2S$ in the sample of nitrogen was linear over a range of 0.2–1300 ppm. The system was optimized for the lowest $H_2S$ concentration by adjusting the two inlet metering valves. The same flow rates and back-pressures were then used for all points. The various samples were introduced in a random sequence so that no memory effect was present. Above 1300 ppm, the signal leveled off rapidly so that even a 10,000 ppm sample showed no substantial increase in signal. This saturation effect is due to the depletion of the $ClO_2$ gas present in the reaction zone per unit time. A higher flow rate (conductance) can be achieved by using a more efficient pump and larger apertures, yet maintaining the pressure $P_2$ of the reaction zone. The calibration curve can then be expected to level out at a higher concentration. At the lowest concentration of 0.2 ppm, the signal is about 40,000 counts/s, while the dark count of the cooled phototube is about 1 count/s. The limit of detection (S/N=3), which commonly refers to the signal to noise ratio, is thus 3 ppb with a response time of 1 s. We note that at low $H_2S$ concentrations (below 100 ppm), no accumulation of sulfur deposits is observed over extended periods of operation, presumably because the products are removed sufficiently rapidly from the reaction zone. This then is a practical upper limit for our particular cell design for continuous monitoring using a single flow setting. Alternately, the cell can be warmed to sublime off the sulfur deposits.

It therefore can be seen that the invention involves a working detector for the continuous monitoring of low levels of hydrogen sulfide and methyl mercaptan, based on chemiluminescence, which is highly selective, so that most common interferences are absent. In fact one would expect that the reaction between chlorine dioxide and $H_2S$ to be suitable for a chemical laser, under the proper conditions.

What is claimed is:

1. A method of generating chemiluminescent light comprising, reacting a gaseous sulfide containing compound selected from the group consisting of hydrogen sulfide and methyl mercaptan with gaseous chlorine dioxide, at a pressure of 40 torr, or lower to provide a single photon of chemiluminescent light for every two molecules of sulfide containing compound.

2. The process of claim 1 wherein the sulfide containing compound is hydrogen sulfide.

3. The process of claim 1 wherein the sulfide containing compound is methyl mercaptan.

* * * * *